United States Patent [19]

Wulfman et al.

[11] Patent Number: 5,584,843
[45] Date of Patent: Dec. 17, 1996

[54] SHAPED WIRE MULTI-BURR ROTATIONAL ABLATION DEVICE

[75] Inventors: Edward I. Wulfman, Woodinville; Thomas J. Clement, Redmond, both of Wash.

[73] Assignee: Boston Scientific Corporation, Redmond, Wash.

[21] Appl. No.: 360,207

[22] Filed: Dec. 20, 1994

[51] Int. Cl.⁶ .................................................. A61B 17/32
[52] U.S. Cl. ................... 606/159; 606/170/180; 604/22
[58] Field of Search ...................... 606/159, 170, 606/180; 128/772; 604/22

[56] References Cited

U.S. PATENT DOCUMENTS

| | | |
|---|---|---|
| 3,309,772 | 6/1964 | Lieb et al. . |
| 3,809,093 | 5/1974 | Abraham . |
| 3,892,117 | 7/1975 | Nelson . |
| 3,937,222 | 2/1976 | Banko . |
| 4,264,307 | 4/1981 | Neuwirth . |
| 4,445,509 | 5/1984 | Auth . |
| 4,729,763 | 3/1988 | Henrie ................................ 604/22 |
| 4,842,579 | 6/1989 | Shiber ................................ 604/22 |
| 4,990,134 | 2/1991 | Auth .................................. 604/22 |
| 5,054,501 | 10/1991 | Chuttani et al. ................... 128/772 |
| 5,085,662 | 2/1992 | Willard ............................. 606/159 |
| 5,112,345 | 5/1992 | Farr ................................. 606/159 |
| 5,226,909 | 7/1993 | Evans et al. . |
| 5,242,460 | 9/1993 | Klein et al. ....................... 606/159 |
| 5,269,793 | 12/1993 | Simpson ........................... 606/159 |
| 5,308,354 | 5/1994 | Zacca et al. ...................... 606/159 |
| 5,312,427 | 5/1994 | Shturman .......................... 606/159 |
| 5,314,407 | 5/1994 | Auth et al. ........................ 604/22 |
| 5,356,418 | 10/1994 | Shturman ........................... 606/159 |
| 5,360,432 | 11/1994 | Shturman ........................... 606/159 |

*Primary Examiner*—Michael Powell Buiz
*Assistant Examiner*—Patrick W. Rasche
*Attorney, Agent, or Firm*—Cowan, Liebowitz & Latman, P.C.

[57] ABSTRACT

The invention is a device for medical applications for differentially cutting abnormal deposits from within a patient's vessels. The device comprises one or more diamond plated burrs or cuffs attached to a flexible drive shaft which rotates at a high speed. The drive shaft is placed over a preformed shaped guidewire so that the drive shaft conforms to the shape of the guidewire, which has been preformed into a gentle "S" or "cork-screw" shape. The guidewire may be rotated at low speed.

29 Claims, 3 Drawing Sheets

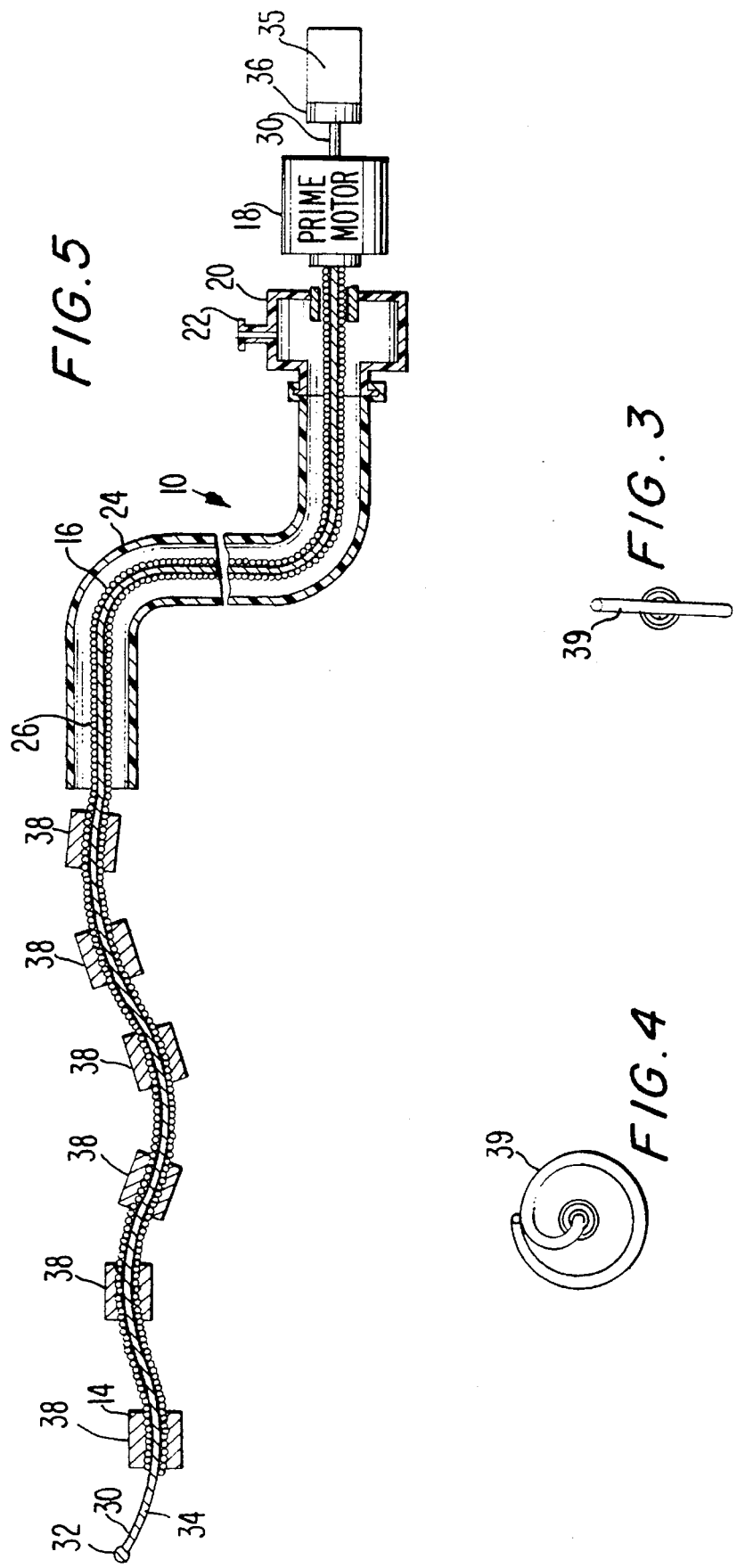

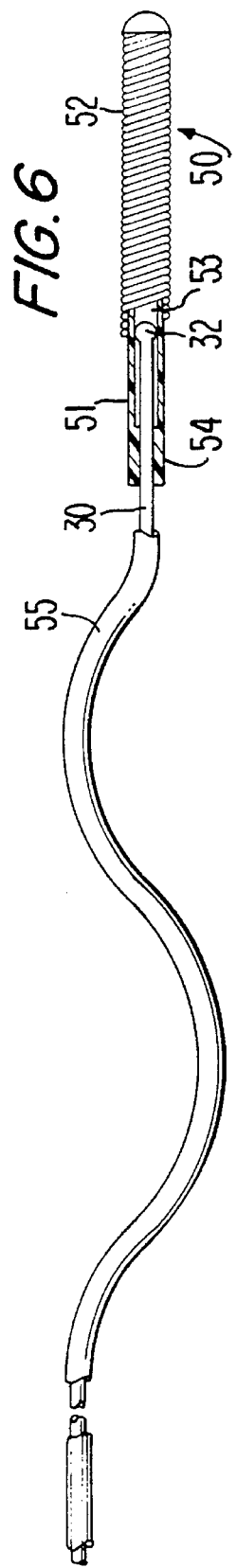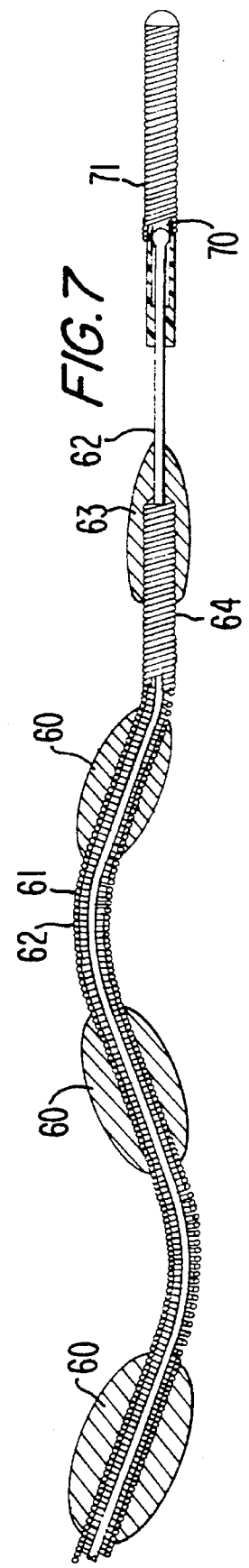

1

SHAPED WIRE MULTI-BURR ROTATIONAL ABLATION DEVICE

FIELD OF THE INVENTION

This invention relates to a mechanical device which is used in medical applications and which is capable of differentially cutting abnormal deposits from within a patient's vessels and which represents an improvement on available art devices.

BACKGROUND OF THE INVENTION

U.S. Pat. No. 4,990,134 entitled TRANSLUMINAL MICRODISSECTION DEVICE, issued to David C. Auth on Feb. 5, 1991, describes a rotating mechanical system which is an improvement upon the invention described in U.S. Pat. No. 4,445,509 entitled METHOD AND APPARATUS FOR REMOVAL OF ENCLOSED ABNORMAL DEPOSITS, issued to David C. Auth on May 1, 1984. The aforesaid U.S. Pat. No. 4,990,134 teaches the use of an ellipsoidal cutting head, or burr, which cutting head is coated with tiny diamond chips (shovels). There the cutting head is taught to rotate at a speed which, in conjunction with its geometrical circumference, provides a surface velocity of at least approximately 40 ft/sec. It is also taught in the '134 patent that a tip (burr) of the type described, operating at such a tip velocity, is able to cut soft material at a high removal rate, while generating microscopic particles (on the order of 5 microns or less) and leaving behind a tissue base having a smooth appearance on the surface of the wall of the vessel from which an abnormal deposit has been removed. The result is due to a principle known as "differential cutting," where a moving or rotating blade can differentiate inelastic material from elastic material.

The atherectomy device taught by the '134 patent, known as the ROTABLATOR® atherectomy device, is marvelously effective at removing plaque. However, this device is not effective to debulk an atherosclerotic arterial lesion to a diameter greater than the diameter of the burr on the drive shaft utilized.

Therefore, there has been a definite need for a rotational ablation device which is capable of debulking the interior of an atherosclerotic artery to a diameter greater than that of the diameter of the burr provided and to do so without unduly adversely impacting upon the interior surface of the wall of the vessel.

SUMMARY OF THE INVENTION

The present invention is an improved rotational ablation device, wherein one or more diamond coated burrs or cuffs are attached to a drive shaft which rotates at a high speed. The drive shaft is placed over a shaped guidewire so that the drive shaft conforms to the shape of the guidewire. The distal portion of the guidewire is preformed into a gentle "S" shape or "cork-screw" shape. The shaped portion of the guidewire is either moved longitudinally within the region of the lesion or rotated slowly, or both, while the burrs or cuffs are rotated at high speed. The device of the present invention has the additional advantage of being able to transmit through smaller guiding catheters, while still being able to debulk larger lumens than is currently possible using prior art devices.

The rotational ablation device of the present invention may be provided with a multiplicity of burrs or cuffs, spaced at intervals along the length of the rotating drive shaft, and is capable of debulking an atherosclerotic arterial or vein lesion such that the final lumen diameter is larger than the diameter of the burr or cuff provided on the drive shaft. Further, due to the nature and the shape of the guidewire provided, the rotational ablation device of the present invention is better suited to carrying out the function of debulking an arterial or vein lesion, in vessels which are greater than the diameter of the burr or cuff, with a minimum of adverse traumatic impact on the vessel walls than known prior art devices.

BRIEF DESCRIPTION OF THE DRAWINGS

FIGS. 3 and 4 each represent a plan view in the proximal direction of the distal portion of the shaped guidewire aspect of the invention;

FIG. 5 is a cross-sectional pictorial view of another embodiment of the present invention, showing the use of abrasive cuffs; and FIGS. 6 and 7 each represent another embodiment of the invention.

DETAILED DESCRIPTION OF THE PREFERRED EMBODIMENT

Figure 1:
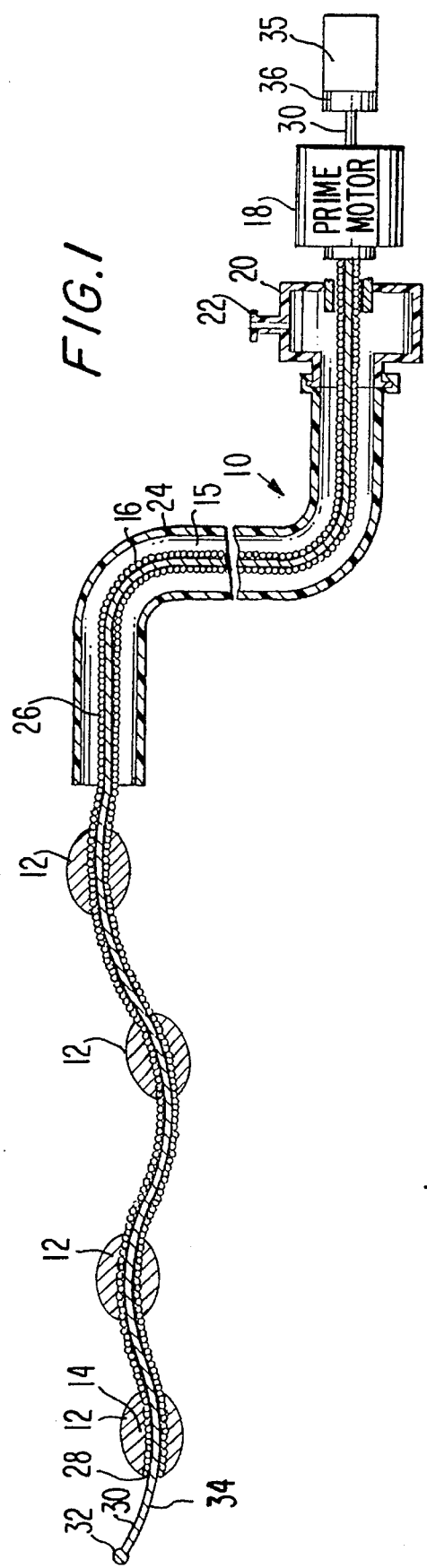
FIG. 1 is a cross-sectional pictorial view of one embodiment of the present invention showing the use of burrs.

Referring generally to FIG. 1, an embodiment 10 of the present invention is shown. The embodiment 10 comprises one or more abrasive burrs 12 and a guidewire 30 with an atraumatic tip 32 which is generally of the type described in U.S. Pat. No. 4,990,134, incorporated herein by reference, and which may be steerable for accessing branch vessels. The burrs 12, which are of a generally ellipsoidal shape, are covered with an abrasive cutting material, such as diamond grit 14, which is used in the preferred embodiment of the invention. The burrs 12 are fixedly attached to a hollow, flexible drive shaft 16, the proximal portion of which is mechanically connected to a high-speed prime mover 18. The proximal portion of guidewire 30 is optionally mechanically attached to an optional low-speed prime mover 35. Each of prime movers 18 and 35 is optionally variable in speed.

Figure 2:
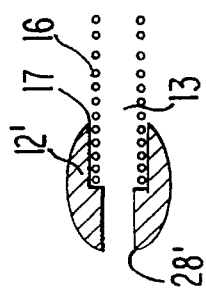
FIG. 2 is a cross-sectional view of an alternate embodiment of the distal portion of the invention.

A preferred embodiment of the distal portion of the flexible drive shaft 16 is shown in FIG. 2, where the distal end 17 of drive shaft 16 extends partly into lumen 28' in distal burr 12'. Preferably distal end 17 extends distally 25 to 80% of the way into lumen 28'. Lumen 28' preferably is counterbored to receive end 17.

In the preferred embodiment of the invention, the drive shaft 16 is from about 0.020" to 0.035" or larger, diameter trifilar helically wound drive shaft. The drive shaft 16 is sealably coupled to an optionally variable speed rotational prime mover 18. The coupling is accomplished using a sealed chamber 20 having an injection port 22, so that injection of drugs or fluids into the lumen 15 which is formed between the drive shaft 16 and a surrounding plastic sheath 24 can be accommodated. The segment 26, or more, of the flexible shaft 16 adjacent to the distal end of the sheath 24 may be passivated with a coating of a low-friction material, such as du Pont's TEFLON® brand polytetrafluoroethylene. The burrs 12 are fixedly attached to the flexible drive shaft 16.

Guidewire tip 32 and shaft 16 are routed into a vessel (not shown) by using a central preformed guidewire 30, which may be comprised of a 0.005" or greater diameter steel wire or hypo tube. The blunt tip 32 may be made from a short, approximately 2.5 cm, hollow tube inside which the body of the wire is captured but not constrained from lateral or rotational motion. Adjacent the blunt tip 32 at the distal end of the guidewire 30, there may be pre-formable portion 34 of the guidewire 30, for example, from 1 to 10 cm, which the physician using the invention may bend to facilitate directing the device into branch vessels. The section 39 of wire proximal to the pre-formable portion 34, from about 10 to 30 cm in length, is pre-formed at the factory in a manner which allows the cutting heads to sweep out a bigger diameter than the diameter of the cutting head. The pre-formed section 39 may be an "S" shape, in a single plane, as shown in FIG. 3, or a corkscrew shape, as shown in FIG. 4, or any other suitable shape. Preferably the pre-formed portion 39 of the guidewire 30 is shaped in a gently curving spiral, which upon viewing from the distal tip of the guidewire appears as a spiral winding.

The guidewire 30 extends completely through the shaft 16 and through prime mover 18 to optional low-speed prime mover 35, which permits the guidewire 30 to be rotated. The drive shaft 16 and the central guidewire 30 may be individually moved with respect to each other and with respect to the plastic sheath 24. The rotational prime mover 18 for the high-speed operation of helical drive shaft 16 is preferably operable in a range of from 10,000 rpm to greater than 160,000 rpm, preferably as high as 190,000 to 225,000 rpm. The low-speed rotational prime mover 35 is preferably operable in a range of 60 or less rpm. Optionally the guidewire can be mechanically attached to a guidewire brake which moves longitudinally with the advancer motion.

The size of the burrs 12 is typically in a range of from less than 1 mm diameter up to about 6 mm, depending upon the vessel size desired where the lesion is being recanalized. The burrs 12 are interspersed along the distal portion of the drive shaft 16 a distance of approximately 1 cm, on center between burrs. Each of the burrs 12 shown is covered with an abrasive cutting material such as diamond grit which is used in the preferred embodiment of the invention. Optionally the distal burr 12 may be of smaller diameter than the other burrs and/or it may have less, or even no, abrasive material on its outer surface.

With reference to FIG. 5, an alternative embodiment of the present invention is shown having a multiplicity of cuffs 38, each of which is located along the length of the flexible drive shaft 16 at intervals of approximately 1 cm on center between cuffs. Each of the cuffs 38 provided is integrally attached to and forms a part of the flexible drive shaft 16 and protrudes a minimum distance from the surface of the flexible drive, to provide the desired cutting action. The distance by which each cuff protrudes from the surface of shaft 16 may vary from about 0.1 mm to about 0.5 mm, or more. The cuffs themselves will vary in over all length from about 1 mm to about 6 mm, depending upon the precise size of the guidewire, the drive shaft diameter, and the intended use of the device. Each of the cuffs 38 shown is covered with an abrasive cutting material such as diamond grit 14, which is used in the preferred embodiment of the invention. Preferably the distal cuff 38 has a rounded, atraumatic distal surface. Optionally distal cuff 38 may instead be similar in shape and function to distal burr 12 described above.

Within the constraints of the device described hereinabove, there are a number of possible variations which may serve to enhance the basic invention in various particular applications, and which are intended to come within the teachings of the present application:

The drive shaft may be of any suitable diameter. A possible variation is to enlarge the drive shaft so that there is less friction between the shaped guidewire and the larger inner diameter of the drive shaft.

The burrs can be of any size or shape that will allow for best debulking. A possible variation, as described in FIG. 4, is to have "cuffs," or short tubes, that are very close in diameter to the diameter of the drive shaft, so in effect the device becomes a cutting drive.

The cuffs may be partially or completely covered in tiny diamond chips, similar to those used on the burrs discussed above, or may be covered with any material that is plateable or adherable to the cuff surface, or may be formed or machined in a manner which is mechanically abrasive.

The burrs can be of any number. In one possible variation, only a single burr is provided on the drive, and the drive is then moved back and forth while the guidewire is turned by hand or some other appropriate means, to enlarge the total cutting area. Alternatively, a plurality of burrs may be used to enlarge the effective cutting area.

The guidewire can be shaped in a number of ways to obtain the most efficient system. One possible variation is to form the distal portion 39 of the guidewire into a gentle "S" shape," in a two-dimensional plane, which would create a shallow wave of a single or multiple wave forms.

The amplitude and wave length of such waves or wave forms can be varied for best performance as will be apparent to one skilled in this art. One variation tested with great success employed an amplitude of approximately 0.125" and wave length of approximately 1.0", with two wave lengths formed in the guidewire.

In another variation, the distal portion 39 of the guidewire may be formed into a corkscrew shape, so that the head-on view of the guidewire forms a circle (See FIG. 4).

The guidewire tip must be atraumatic. One contemplated variation of the guidewire tip is a coil or tube of a larger diameter than that of the guidewire, so that the guidewire can slide inside. This guidewire configuration would allow the guidewire form to travel longitudinally with the drive shaft or rotationally independent of the drive shaft during advancer operation, while the tip of the guidewire stays immobile at the distal end of the lesion.

The main body of the guidewire may be of variable geometry to obtain the correct torque and spring effect, as will be required for different clinical situations, as will be apparent to one skilled in this art.

One embodiment contemplated comprises providing a stainless steel guidewire of 0.010" diameter that would be reduced to 0.008" diameter, where the distal wave form is located. This would serve to provide strength over the main body of the wire for rotation (torquing) and yet at the wave form, the smaller wire diameter would provide the correct spring effect and also allow the drive to move over the curved section more easily. The guidewire could also be comprised of other metals conventionally used in guidewires, such as nitinol or another medically acceptable alloy.

Another embodiment comprises a guidewire which is a combination of a shaped hypo tube where the distal end of the hypo tube has a pre-formed "S" or cork-screw shape. The hypo tube would be threaded into a vessel over a straight, small diameter guidewire. This would serve to facilitate steering of the shaped wire to the lesion site by allowing placement of the small diameter straight wire across the lesion first.

In one variation of the cutting action contemplated using the device of the present invention, the drive shaft and guidewire would move as one unit during the cutting operation. This would be accomplished as follows:

1. The guidewire having a pre-formed shape at its distal end is placed across the lesion, possibly using an exchange catheter and guidewire combination.
2. The drive catheter is advanced over the guidewire until it is placed proximal to the lesion.
3. The guidewire and drive shaft are adjusted so that the burrs are located over the guidewire's wave form.
4. The catheter and guidewire are advanced as one unit across the lesion in back and forth motion while the burrs are spinning at high speed. The guidewire moves longitudinally with the drive shaft, but does not rotate. This would require a guidewire brake which moves longitudinally with the advancer motion.

The advantage of this system is that the guidewire does not need to be manipulated during (or between) cutting actions.

In a second possible variation of the cutting action contemplated using the device of the present invention, the drive shaft is moved over the shaped guidewire during the cutting action. This would be accomplished as follows:

1. The guidewire is placed across the lesion, possibly using an exchange catheter and guidewire combination.
2. The guidewire is placed across lesion so that the pre-formed shape is located across the lesion area to be cut.
3. The drive catheter is advanced over the guidewire until it is located just proximal to the lesion.
4. The drive shaft with burrs is advanced across the lesion over the guidewire, with the guidewire stationary. This would be accomplished using an advancer motion, as is done currently in conventional rotational ablation procedures.
5. Between cutting actions, the guidewire would be rotated or advanced so that a complete round channel is cut.

The foregoing procedure has the advantage that the guidewire does not move during advancer action.

In a third variation of the cutting action contemplated using the device of the present invention, the drive shaft advances and rotates and the guidewire rotates but does not advance during the cutting operation. This would be accomplished as follows:

1. The guidewire having a pre-formed shape at its distal end is placed across the lesion, possibly using an exchange catheter and guidewire combination.
2. The drive catheter is advanced over the guidewire until it is placed proximal to the lesion.
3. The guidewire is rotated at low speed.
4. The drive shaft is advanced across the lesion in back and forth motion while the burrs are spinning at high speed.

According to a fourth variation, the drive shaft and guidewire advance together with both rotating at high and low speeds, respectively.

Another embodiment of the invention concerns a guidewire or shaped wire wherein the distal portion optionally comprises a flexible, formable tip. As shown in FIG. 6, the distal tip 32 of the guidewire 30 may be encased in a flexible, formed tip 50. Tip 50 comprises a tubular section 51 and a spring portion 52, where the distal tip 32 is received in a bore 53. The proximal portion 54 of bore 53 is smaller than its main portion to retain distal tip 32. Here, shaped tube 55 concentrically surrounds, and gives an "S" shape to, guidewire 30.

In the embodiment of the distal portion shown in FIG. 7, burrs 60 are fixedly attached to flexible drive shaft 61, which is positioned around pre-formed guidewire 62. Distal burr 63 caps the distal portion 64 of flexible shaft 61, and guidewire 62 extends distally through burr 63 into bore 70 within flexible tip 71. This arrangement permits guidewire 62 to spin at low speed and move longitudinally while guidewire tip 71 rotates slowly or hardly at all.

The description above is primarily directed to use of the apparatus of the invention in removing stenotic material from an artery. One skilled in the art would appreciate that this apparatus would also be effective in removing material from other physiologic channels.

It will be further apparent to one skilled in this art that the improvements provided for in the present invention, while described with relation to certain specific physical embodiments also lend themselves to being applied in other physical arrangements not specifically provided for herein, which are within the spirit and scope of the invention taught here.

Further, the preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A shaped wire rotational ablation system comprising:
   (a) a shaped guidewire having proximal and distal portions, the distal portion of the shaped guidewire being preformed into a corkscrew shape or a gentle "S" shape curve;
   (b) a flexible, hollow drive shaft defining a lumen and having a rotatable abrasive tip attached thereto, said tip having a diameter which is greater than that of said drive shaft and said tip having a substantially cylindrical opening in fluid communication with said drive shaft lumen so that said drive shaft and tip can be guided along said guidewire, said drive shaft having affixed along the distal portion thereof a multiplicity of cutting surfaces;
   (c) an abrasive surface on said cutting surfaces, said abrasive surface being comprised of abrasive material imbedded in, attached to, or machined from said tip; and
   (d) a rotatable prime mover which is capable of rotating said drive shaft at a rotation rate of from about 10,000 revolutions per minute to as high as about 225,000 revolutions per minute, whereby said abrasive material microdissects particles small enough to pass through the capillaries of a person.

2. The shaped wire rotational ablation device of claim 1 further comprising a tubular sheath which surrounds said flexible drive shaft and chamber means for sealably attaching to said tubular sheath, said chamber means sealably attaching to said tubular sheath and said chamber means including a seal through which said drive shaft passes.

3. The shaped wire rotational ablation device of claim 1, wherein the multiplicity of cutting surfaces affixed along the distal portion of the drive shaft are in the form of burrs which are generally ellipsoidal in shape and are affixed in spaced apart fashion along the length of the distal portion of the drive shaft.

4. The shaped wire rotational ablation device of claim 1, wherein the multiplicity of cutting surfaces affixed along the distal portion of the drive shaft are in the form of cuffs which are generally cylindrical in shape and are affixed in spaced apart fashion along the length of the distal portion of the drive shaft.

5. The shaped wire ablation device of claim 1, wherein the multiplicity of cutting surfaces are affixed along the length of the distal portion of the drive shaft and are spaced apart approximately from about 0.5 to 5.0 cm on center.

6. The shaped wire rotational ablation device of claim 1, wherein the distal portion of the drive shaft has affixed thereto a multiplicity of generally ellipsoidal shaped abrasive cutting surfaces each of which is from about 1 mm to about 6 mm in diameter.

7. The shaped wire rotational ablation device of claim 1, wherein the distal portion of the drive shaft has affixed thereto a multiplicity of generally cylindrical shape abrasive cutting cuffs each of which protrudes above the surface of the drive shaft a distance of from about 0.1 mm to about 0.5 mm, and vary in length from about 1 mm to about 6 mm.

8. The shaped wire rotational ablation device of claim 1, wherein at least a portion of the multiplicity of cutting surfaces are covered with diamond grit.

9. The shaped wire rotational ablation device of claim 1, wherein the drive shaft is approximately 0.026" diameter trifilar helically wound drive shaft.

10. The shaped wire rotational ablation device of claim 1, wherein the distal portion of the guidewire is preformed into a gentle "S" shape which when viewed in a two dimensional plane would create a shallow wave of single or multiple wave forms.

11. The shaped wire rotational ablation device of claim 1, wherein the distal portion of the guidewire is preformed to create a shallow multiple wave form having an amplitude of approximately 0.125" and a wave length of approximately 1.0".

12. The shaped wire rotational ablation device of claim 1, wherein the guidewire is fabricated of stainless steel which is approximately 0.010" in diameter and the distal portion thereof is shaped into a gentle "S" shape or cork-screw shape wherein the diameter of the guidewire is reduced to approximately 0.008" in diameter in that portion of the guidewire where a wave form is located.

13. The shaped wire rotational ablation device of claim 1, wherein the guidewire has a distal atraumatic wire tip which is a hollow coil or tube which is captive on the guidewire but allows the guidewire to freely rotate or move longitudinally within the coil or tube.

14. The shaped wire rotational ablation device of claim 1, wherein the abrasive tip is substantially ellipsoidal.

15. The shaped wire rotational ablation device of claim 1, wherein the proximal portion of the guidewire is attached to a rotatable prime mover for rotating the guidewire.

16. The shaped wire rotational ablation device of claim 1, wherein the proximal portion of the guidewire is attached to a guidewire brake that can move longitudinally in concert with the high speed prime mover.

17. The shaped wire rotational ablation device of claim 1 further comprising a tubular sheath which surrounds said flexible drive shaft and chamber means for sealably attaching to said tubular sheath, said chamber means including a seal through which said drive shaft passes.

18. A shaped wire rotational ablation system comprising:
 (a) a substantially linear guidewire having proximal and distal ends;
 (b) a shaped hypotube having proximal and distal portions, the distal portion of the shaped hypo tube being pre-formed into a corkscrew shape or a gentle "S" shape curve and the shaped hypo tube fitting slidingly over the guidewire;
 (c) a flexible, hollow drive shaft defining a lumen and having a rotatable abrasive tip attached thereto, said tip having a diameter which is greater than that of said drive shaft and said tip having a substantially cylindrical opening in fluid communication with said drive shaft lumen so that said drive shaft and tip can be guided along said guidewire and said shaped hypo tube, said drive shaft having affixed along the distal portion thereof a multiplicity of cutting surfaces;
 (d) an abrasive surface on said cutting surfaces, said abrasive surface being comprised of abrasive material imbedded in, attached to, or machined from said tip; and
 (e) a rotatable prime mover which is capable of rotating said drive shaft at a rotation rate of from about 10,000 revolutions per minute to as high as about 225,000 revolutions per minute, whereby said abrasive material microdissects particles small enough to pass through the capillaries of a person.

19. The shaped wire rotational ablation device of claim 18, wherein the multiplicity of cutting surfaces affixed along the distal portion of the drive shaft are in the form of burrs which are generally ellipsoidal in shape and are affixed in spaced apart fashion along the length of the distal portion of the drive shaft.

20. The shaped wire rotational ablation device of claim 19, wherein each of the generally ellipsoidal shaped abrasive cutting surfaces is from about 1 mm to about 6 mm in diameter.

21. The shaped wire rotational ablation device of claim 18, wherein the multiplicity of cutting surfaces affixed along the distal portion of the drive shaft are in the form of cuffs which are generally cylindrical in shape and are affixed in spaced apart fashion along the length of the distal portion of the drive shaft.

22. The shaped wire rotational ablation device of claim 21, wherein each of the generally cylindrically shaped abrasive cutting cuffs protrudes above the surface of the drive shaft a distance of from about 0.1 mm about to 0.5 mm, and vary in length from about 1 mm to about 6 mm.

23. The shaped wire ablation device of claim 18, wherein the multiplicity of cutting surfaces are affixed along the length of the distal portion of the drive shaft and are spaced apart approximately from about 0.5 to 5.0 cm on center.

24. The shaped wire rotational ablation device of claim 18, wherein at least a portion of the multiplicity of cutting surfaces are covered with diamond grit.

25. The shaped wire rotational ablation device of claim 18, wherein the drive shaft is approximately 0.026" diameter trifilar helically wound drive shaft.

26. A method of removing a stenotic lesion in a corporal vessel, which comprises the steps of:
 (a) advancing the distal end of a guidewire into a vessel until the distal end of the guidewire is adjacent to or distal to the lesion;
 (b) threading distally over the guidewire a hypo tube wherein the distal end of the hypo tube has a pre-formed, corkscrew shape or a gentle "S" shape curve, until the distal end of the hypo tube is positioned across the lesion;
 (c) threading distally over the hypo tube a flexible drive shaft having one or more cutting surfaces arranged on the exterior surface of its distal portion, until the distal end of the flexible drive shaft is proximal to the lesion; and (d) rotating the flexible drive shaft or both the flexible drive shaft and the shaped hypotube while longitudinally moving the drive shaft and optionally the guidewire to cause the cutting surface to cut into the lesion to create microparticles.

27. A method of removing a stenotic lesion in a corporal vessel, which comprises the steps of:

(a) advancing the distal end of a guidewire into a vessel until the distal end of the guidewire is adjacent to or distal to the lesion, the distal portion of the guidewire being pre-formed into a corkscrew shape or a gentle "S" shape curve;

(b) threading distally over the guidewire a flexible drive shaft having one or more cutting surfaces arranged on the exterior surface of its distal portion, until the distal end of the flexible drive shaft is proximal to the lesion; and (c) rotating the flexible drive shaft or both the flexible drive shaft and the shaped guidewire while longitudinally moving the drive shaft and optionally the guidewire to cause the cutting surface to cut into the lesion to create microparticles.

28. A shaped wire rotational ablation system comprising:

(a) a shaped guidewire having proximal and distal portions, the distal portion of the shaped guidewire being pre-formed into a non-linear shape;

(b) a flexible, hollow drive shaft defining a lumen and having a rotatable abrasive tip attached thereto, said tip having a diameter which is greater than that of said drive shaft and said tip having a substantially cylindrical opening in fluid communication with said drive shaft lumen so that said drive shaft and tip can be guided along said guidewire, said drive shaft having affixed along the distal portion thereof a multiplicity of cutting surfaces;

(c) an abrasive surface on said cutting surfaces, said abrasive surface being comprised of abrasive material imbedded in, attached to, or machined from said tip;

(d) a rotatable prime mover attached to the proximal portion of the guidewire for rotating the guidewire; and (e) a rotatable prime mover which is capable of rotating said drive shaft at a rotation rate of from about 10,000 revolutions per minute to as high as about 225,000 revolutions per minute, whereby said abrasive material microdissects particles small enough to pass through the capillaries of a person.

29. A shaped wire rotational ablation system comprising:

(a) a shaped guidewire having proximal and distal portions, the distal portion of the shaped guidewire being pre-formed into a non-linear shape;

(b) a flexible, hollow drive shaft defining a lumen and having a rotatable abrasive tip attached thereto, said tip having a diameter which is greater than that of said drive shaft and said tip having a substantially cylindrical opening in fluid communication with said drive shaft lumen so that said drive shaft and tip can be guided along said guidewire, said drive shaft having affixed along the distal portion thereof a multiplicity of cutting surfaces;

(c) an abrasive surface on said cutting surfaces, said abrasive surface being comprised of abrasive material imbedded in, attached to, or machined from said tip;

(d) a rotatable prime mover which is capable of rotating said drive shaft at a rotation rate of from about 10,000 revolutions per minute to as high as about 225,000 revolutions per minute, whereby said abrasive material microdissects particles small enough to pass through the capillaries of a person; and (e) a guidewire brake attached to the proximal portion of the guidewire, wherein said guidewire brake can move longitudinally in concert with the rotatable prime mover.

* * * * *